United States Patent
Belbekhouche et al.

(10) Patent No.: US 11,357,735 B2
(45) Date of Patent: Jun. 14, 2022

(54) PARTICLES AND COMPOSITIONS COMPRISING THE SAME FOR TRANSFECTION

(71) Applicants: CENTRE NATIONAL DE LA RECHERCHE SCIENTIFIQUE, Paris (FR); UNIVERSITE PARIS-EST CRETEIL VAL DE MARNE, Creteil (FR); INSTITUT NATIONAL DE LA SANTE ET DE LA RECHERCHE MEDICALE, Paris (FR); ASSISTANCE PUBLIQUE—HOPITAUX DE PARIS, Paris (FR)

(72) Inventors: Sabrina Belbekhouche, Valenton (FR); André Pawlak, Saint Maur des Fosses (FR); Djillali Sahali, Sceaux (FR); Benjamin Carbonnier, Groffliers (FR)

(73) Assignees: Centre National De La Recherche Scientifique; Universite Paris-Est Cretreil Vai De Marne; Institut National De La Sante Et De La Recherche Medicale; Assistance Piklinne—Hopitaux De Paris

( * ) Notice: Subject to any disclaimer, the term of this patent is extended or adjusted under 35 U.S.C. 154(b) by 0 days.

(21) Appl. No.: 16/484,775

(22) PCT Filed: Feb. 1, 2018

(86) PCT No.: PCT/EP2018/052553
§ 371 (c)(1),
(2) Date: Aug. 8, 2019

(87) PCT Pub. No.: WO2018/141865
PCT Pub. Date: Aug. 9, 2018

(65) Prior Publication Data
US 2020/0038336 A1 Feb. 6, 2020

(30) Foreign Application Priority Data
Feb. 1, 2017 (EP) ..................... 17305115

(51) Int. Cl.
*A61K 9/50* (2006.01)
*A61K 47/69* (2017.01)
*A61K 9/51* (2006.01)
*C12N 15/113* (2010.01)

(52) U.S. Cl.
CPC .......... *A61K 9/5078* (2013.01); *A61K 9/5036* (2013.01); *A61K 9/5192* (2013.01); *A61K 47/6925* (2017.08); *A61K 47/6929* (2017.08); *C12N 15/113* (2013.01); *C12N 2310/14* (2013.01); *C12N 2320/32* (2013.01)

(58) Field of Classification Search
CPC .............. C12N 15/113; C12N 2310/14; C12N 2320/32; A61K 47/6923; A61K 47/6929; A61K 49/00; A61K 49/0002; A61K 31/00; A61K 47/645
USPC ...... 424/9.1; 435/6.1, 91.1, 91.31, 455, 458; 536/23.1, 24.5; 514/44 A, 44 R
See application file for complete search history.

(56) References Cited

U.S. PATENT DOCUMENTS

| 879,312 | A | 2/1908 | Perry | |
| 2019/0091163 | A1* | 3/2019 | Craster | .................. A61K 38/04 |

FOREIGN PATENT DOCUMENTS

| WO | WO-0052023 A1 * | 9/2000 | ......... C07K 16/2803 |
| WO | 2007/086923 | 8/2007 | |
| WO | WO-2007086923 A2 * | 8/2007 | ......... A61K 48/0041 |

OTHER PUBLICATIONS

Han et al (Nano, vol. 6, No. 8, pp. 7340-7351 (2012)) (Year: 2012).*
Ye et al (J. Biomater. Sci. Polymer Edn., vol. 16, No. 7, pp. 909-923 (2005)) (Year: 2005).*
Moktefi et al (Kidney Int'l, vol. 90, pp. 1298-1311 (2016)) (Year: 2016).*
The International Search Report (ISR) for PCT/EP2018/052553 dated Mar. 14, 2018, pp. 1-5.
Written Opinion of the International Searching Authority for PCT/EP2018/052553 dated Mar. 14, 2018, pp. 1-5.
Ye, Shiqu et al. "Multilayer nanocapsules of polysaccharide chitosan and alginate through layer-by-layer assembly directly on PS nanoparticles for release" Journal of Biomaterials Science (2005) vol. 16(7), pp. 909-923.
Huan, Lu et al. "Enhanced siRNA Delivery and Silencing Gold-Chitosan Nanosystem with Surface Charge-Reversal Polymer Assembly and Good Biocompatibility" ACS Nono (2012) vol. 6(8), pp. 7340-7351.

* cited by examiner

*Primary Examiner* — Jane J Zara
(74) *Attorney, Agent, or Firm* — McDonnell Boehnen Hulbert & Berghoff LLP

(57) ABSTRACT

The present invention relates to the localized delivery of nucleic acids to cells using polyelectrolyte assemblies in the form of particles that are prepared by layer-by-layer deposition of nucleic acid and specific polycation. It also relates to compositions comprising said particles and methods for the treatment of disorders or diseases by administration of such particles.

Figure 1:
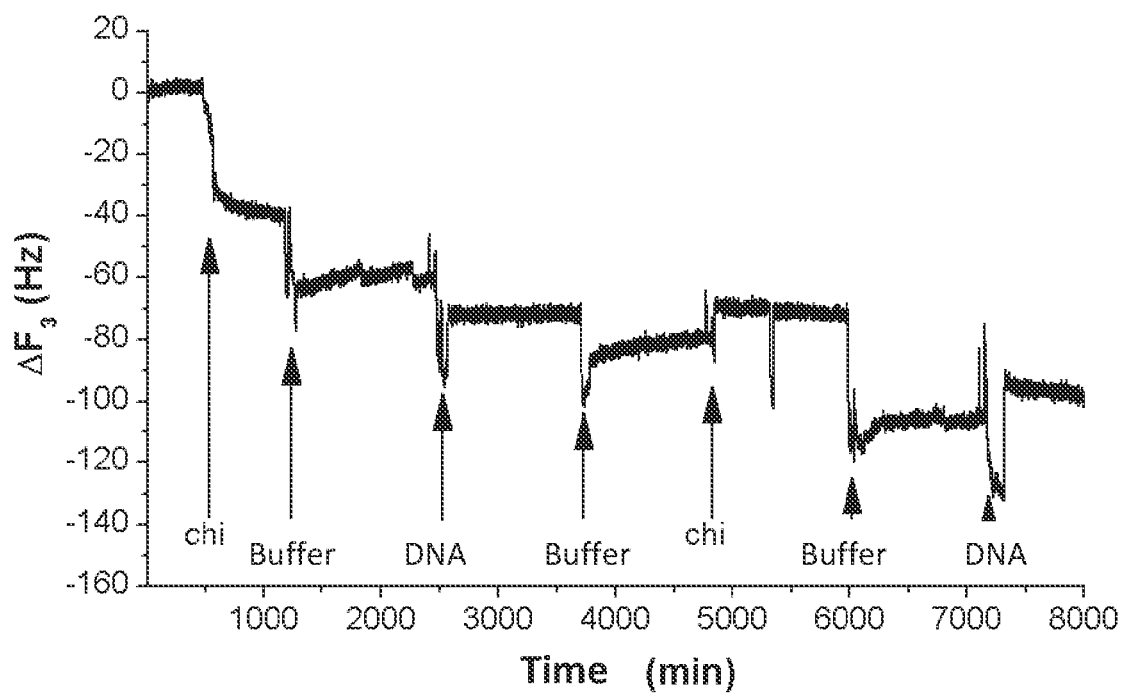

9 Claims, 6 Drawing Sheets
Specification includes a Sequence Listing.

```
SEQUENCE LISTING

<160> NUMBER OF SEQ ID NOS: 3

<210> SEQ ID NO 1
<211> LENGTH: 64
<212> TYPE: DNA
<213> ORGANISM: artificial
<220> FEATURE:
<223> OTHER INFORMATION: G6 sequence

<400> SEQUENCE: 1
tgctgtgagg atcttgctga gaaagggttt tggccactga ctgacccttt ctccaagatc      60
ctca                                                                  64

<210> SEQ ID NO 2
<211> LENGTH: 64
<212> TYPE: DNA
<213> ORGANISM: artificial
<220> FEATURE:
<223> OTHER INFORMATION: G8 sequence

<400> SEQUENCE: 2
tgctgtgttg atgaactctt catagcgttt tggccactga ctgacgctat gaagttcatc      60
aaca                                                                  64

<210> SEQ ID NO 3
<211> LENGTH: 61
<212> TYPE: DNA
<213> ORGANISM: artificial
<220> FEATURE:
<223> OTHER INFORMATION: scramble sequence

<400> SEQUENCE: 3
tgctgaaatg tactgcgcgt ggagacgttt tggccactga ctgacgtctc cacgcagtac      60
a                                                                     61
```

PARTICLES AND COMPOSITIONS COMPRISING THE SAME FOR TRANSFECTION

CROSS-REFERENCE TO RELATED APPLICATIONS

This application is a U.S. national phase of International Application No. PCT/EP2018/052553, filed Feb. 1, 2018, which claims priority from European patent application no. 17305115.2, filed Feb. 1, 2017, the disclosure of each of which is hereby incorporated by reference in its entirety.

FIELD OF THE INVENTION

This invention relates generally to the field of nucleic acid delivery into cells (i.e., transfection). More particularly, the present invention relates to the localized delivery of nucleic acids to cells using polyelectrolyte assemblies in the form of particles that are prepared by layer-by-layer deposition of nucleic acid and specific polycation. It also relates to compositions comprising said particles and methods for the treatment of disorders or diseases by administration of such particles.

BACKGROUND OF THE INVENTION

Thin films and coatings that sustain the release of DNA from surfaces are playing an important role in the development of localized approaches to gene therapy. In that context, attempts have been made to provide implantable devices coated with polyelectrolyte assemblies comprising nucleic acids and polycations, such as poly(beta-amino ester)s, poly(4-hydroxy-L-proline ester), poly[alpha-(4-aminobutyl)-L-glycolic acid], and combinations thereof (see US2006/0251701). However, such polycations cannot be readily modified to present satisfactory targeting and/or transfection properties. Also, it has been described viral vectors or non-viral vectors, carrying specific RNAs nanoparticles (RNAs stands for ribonucleic acid molecules), for gene therapy, where said vectors are complexed or linked to polymers as to stabilize the vectors, and more specifically RNAs, or to assist in their targeting (see, for instance, WO2013/063019). However, said nanoparticles can present a wide range of sizes which cannot be easily controlled and quality and quantity of incorporated RNAs cannot be tuned in view of the producing process. Finally, WO 2015/088445 discloses methods for the delivery of intact RNA to a target site by providing a multilayered nanoparticle for delivery of RNA to a cell, the nanoparticle comprising: a core nanoparticle coated by alternating positively and negatively charged polymer layers, wherein at least one of the negatively charged polymer layers comprises or consist of RNA. The negatively and positively charged polymer layers can be different types of polymers, and more specifically dextran sulfate and poly L-arginine, respectively. This reference does not however describe delivery of DNA from vectors. It has been previously shown that C-Maf inducing protein (CMIP) is overproduced in podocyte diseases and alters intracellular signaling. CMIP is a gene that encodes an 86 kDa protein which is scarcely or undetected in normal glomeruli. There is growing evidence that increased CMIP abundance could dramatically affect the function and survival of podocytes. Podocyte damage plays a central role in the pathogenesis of idiopathic nephrotic syndrome, as well as in the progression of many chronic glomerular diseases. Idiopathic nephrotic syndrome (INS) defines several entities, including minimal change nephrotic syndrome (MCNS) and focal and segmental glomerulosclerosis (FSGS) which are considered to be prototypic podocyte diseases. Podocytes are terminally differentiated cells that line the outer aspect of the glomerular basement membrane and constitute the ultimate barrier to urinary protein loss by the formation and maintenance of the podocytes foot processes and the interposed slit diaphragm. Podocytes diseases might result from genetic defects of proteins playing a key structural and/or regulatory role in the integrity of the glomerular filtration barrier. Podocytes diseases, such as MCNS, are glomerular diseases characterized by heavy proteinuria. For instance, MCNS is a glomerular disease characterized by a heavy proteinuria with a relapsing/remitting course without histological evidence of classical immune mechanisms mediated injury. In vivo studies have also shown that silencing endogenous CMIP with siRNA prevents the induction of proteinuria in LPS-treated mice. Podocytes are also cells known to be difficult to target. A few articles relating to use of virus based expression vectors into podocytes show very low positive cells percentages and low expression rate within infected cells. Virus based expression vectors are therefore not suitable for efficient gene therapy into podocytes.

The present invention here aims at providing nanoparticles comprising DNA expression vectors produced by layer-by layer deposition. Such nanoparticles present several advantages. They can be readily formulated in injectable solutions. The nanoparticles of the invention can target specific cells, such as podocytes, allowing thereby efficient nucleic acid delivery and expression thereof into said cells in a controlled manner. More specifically, nanoparticles comprising DNA non-viral expression vectors encoding RNA interference (iRNA) able to silence CMIP mRNA have been prepared by layer-by-layer deposition of such DNA expression vectors and specific polycation. In vitro studies have been performed with said nanoparticles on HEK (Human Embryonic Kidney cells) transfected with a mouse CMIP expressing vector, and CMIP silencing was obtained.

SUMMARY OF THE INVENTION

The invention provides therefore a therapeutic strategy for the treatment of disorders, such as podocytes disorders, by transfecting cells with nanoparticles of the invention allowing thereby delivering a therapeutic gene material and its associated regulatory elements into the cells, in order to correct the loss of function caused by mutation or to express a deficient gene product at physiologic levels or to prevent over-expression of a deleterious gene. Moreover, the present invention provides a method of promoting delivery of a nucleic acid to a cell. Such method includes the step of contacting a cell with nanoparticles that are fabricated by layer-by-layer deposition of non-viral expression DNA vector and specific polycation, i.e., chitosan derivative, upon any suitable substrate, wherein the vector is directly and locally-delivered to the cell upon degradation or physical erosion of the polycation.

The present invention relates to a nanoparticle comprising a nanoparticle core and a multilayered shell, wherein:
  said multilayer shell is composed of at least one alternate bilayer of one positively charged layer comprising at least one chitosan derivative and of one negatively charged layer comprising or consisting of at least one non-viral expression DNA vector, where the outer layer of the multilayer shell is a positively charged layer comprising said at least one chitosan derivative, and said chitosan derivatives are thiolated chitosan derivatives or a mixture of thiolated chitosan derivatives and non thiolated chitosan derivatives In another aspect, the invention relates to a pharmaceutical composition comprising nanoparticles of the invention and a pharmaceutically acceptable carrier.

Nanoparticles or pharmaceutical compositions of the invention are for use in the treatment of disorders or diseases by gene therapy.

Nanoparticles or pharmaceutical compositions of the invention are more specifically for use in the treatment of a podocyte disease, wherein the said at least one non-viral expression DNA vector encodes at least one interfering RNA capable of silencing CMIP.

Another aspect of the present invention relates to a method for the treatment of podocyte disease, wherein nanoparticles or pharmaceutical compositions of the invention are administered to a subject in need of such treatment, and wherein the said at least one non-viral expression DNA vector encodes at least one interfering RNA capable of silencing CMIP.

According to a further embodiment, the invention deals with a method for the preparation of nanoparticles of the invention, comprising the steps consisting of:
a. providing a core nanoparticle, as a template, that comprises or consists of a material selected from the group consisting of metals, metal-coated materials, metal oxides, plastics, ceramics, silicon, glasses, mica, graphite, hydrogels, polymers and combinations thereof, preferably the material is gold,
b. at least one step of layer-by-layer depositing alternatively a positively charged layer comprising at least one chitosan derivative and a negatively charged layer comprising or consisting of at least one non-viral expression DNA vector, on the surface of the core of step (a) to provide a polyelectrolyte assembly coating on the surface of the core, where the last deposited layer is a positively charged layer comprising said at least one chitosan derivative,
where said chitosan derivatives of the polyelectrolyte assembly are thiolated chitosan derivatives or a mixture of thiolated chitosan derivatives and non thiolated chitosan derivatives, optionally, destruction of the material of step (a).

Another aspect relates to a target cell, which is transfected or transduced with the nanoparticle as herein described.

Other aspects and embodiments of the invention will be apparent in the following detailed description.

LEGENDS OF THE FIGURES

FIG. 1. Variation of the frequency ($\Delta F_3$ (Hz)) during the formation of the multilayer film (time in minutes) on a flat gold surface with an alternate bilayer of one positively charged layer comprising at least one chitosan derivative (chi) and one negatively charged layer comprising at least one non-viral expression DNA vector (DNA). A buffered solution (Buffer) is used between each deposited layer.

Figure 2:
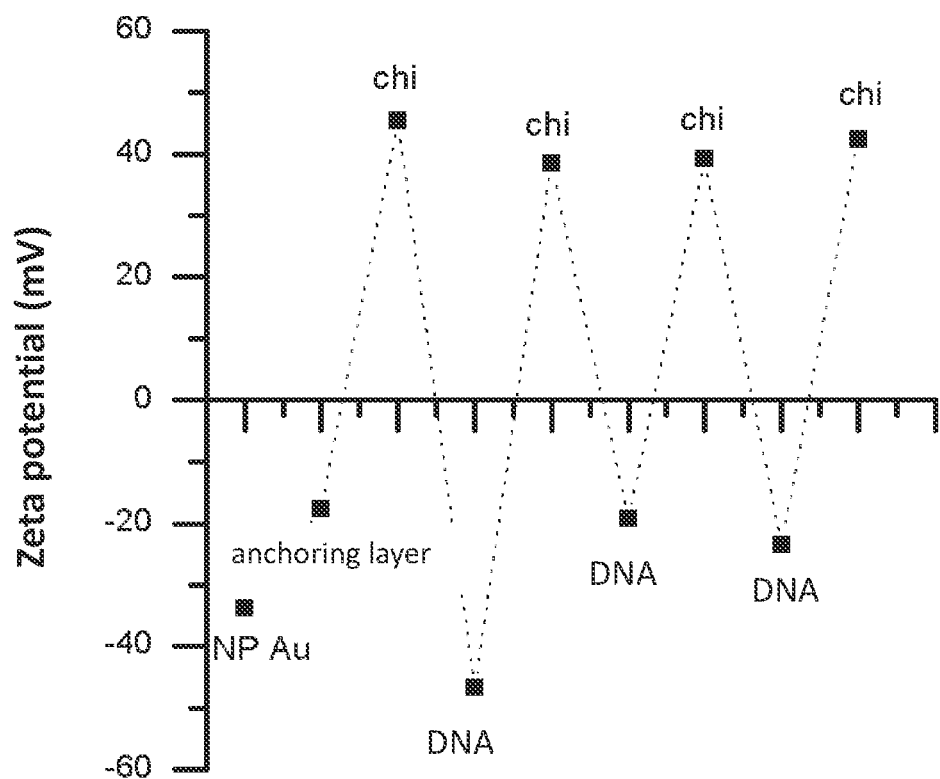

FIG. 2. Evolution of the zeta potential (mV) during the sequential deposition of chitosan (chi) and DNA vector (DNA) on the gold nanoparticle (NP Au) with an anchoring layer.

Figure 3:
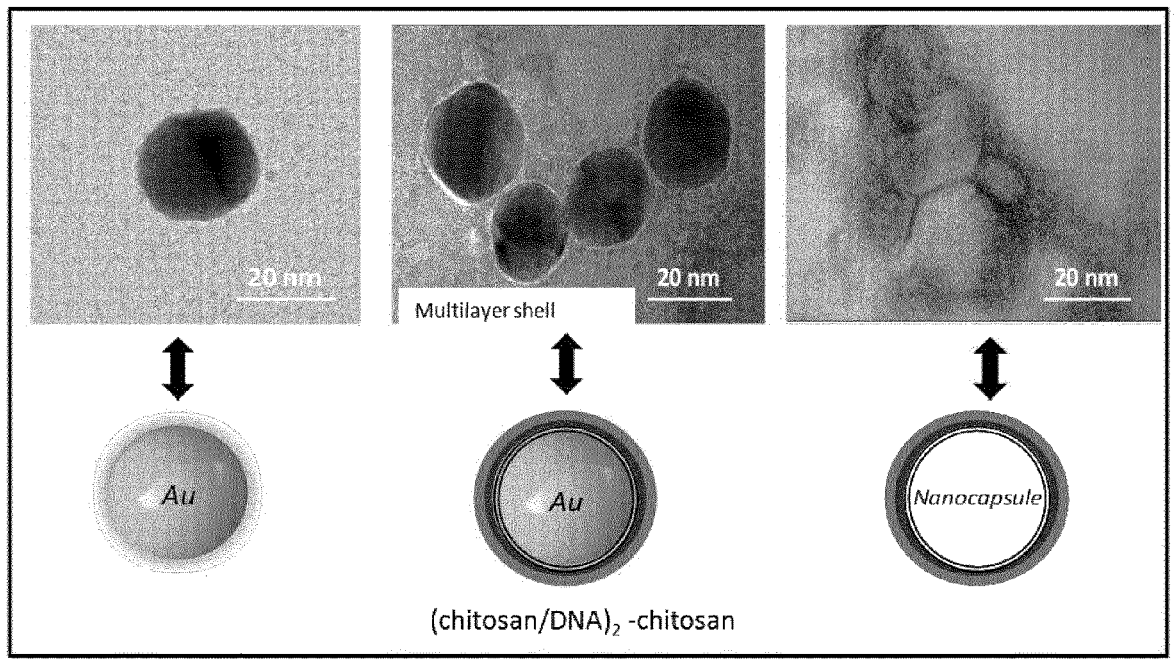

FIG. 3. Pictures from Transmission Electron Microscopy (TEM) showing a gold matrix (left picture: template), a nanoparticle comprising the gold matrix, an alternate bilayer of chitosan and DNA vector coated to the template (gold matrix) and an outer layer of chitosan coated to the alternate bilayer (middle picture), a nanoparticle with an alternate bilayer of chitosan and DNA vector coated to the template and an outer layer of chitosan coated to the alternate bilayer. The nanoparticle core is hollow, more precisely without the gold matrix (right picture).

Figure 4:
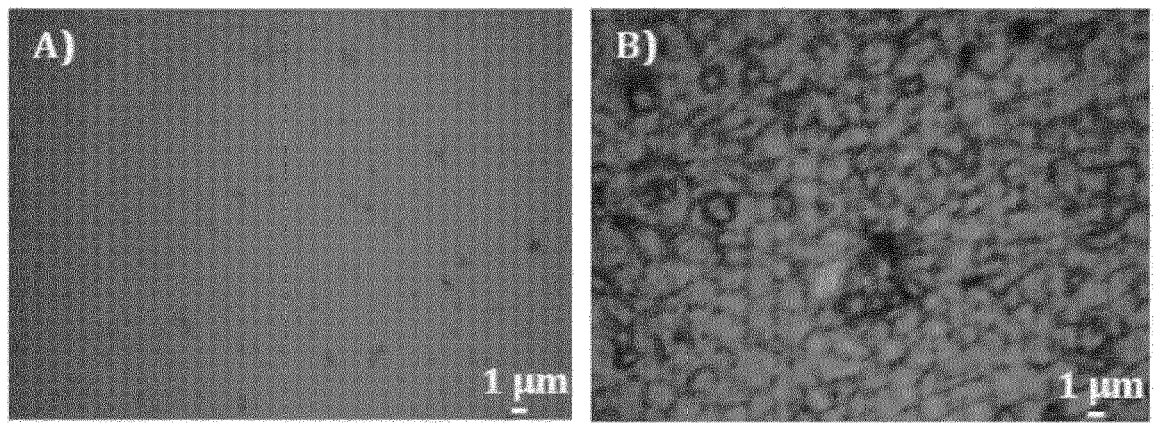

FIG. 4. Experiments of cellular adhesion (HEK cells) on (A) bare flat surface of gold and (B) on flat surface of gold modified with an alternate bilayer of chitosan and DNA vector and an outer layer of chitosan.

Figure 5:
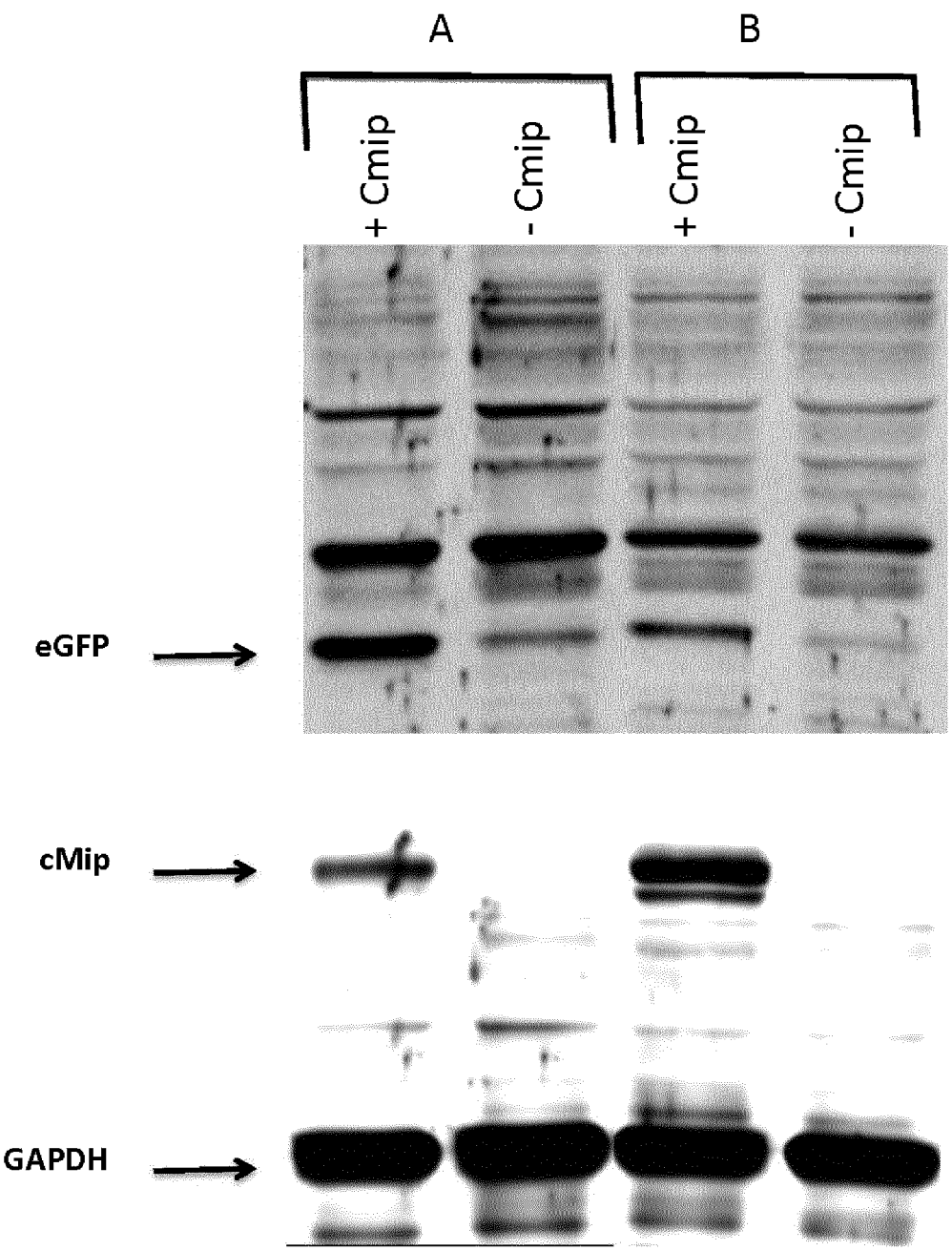

FIG. 5. Nanoparticles comprising eGFP as control sequence and anti Cmip sequences were tested in culture with HEK cells transfected (+Cmip) or not (−Cmip) with a mouse Cmip expression vector. (A) 150 µl nanoparticles (5 $10^9$/ml); (B) 50 µl nanoparticles (5·$10^9$/ml).

Figure 6:
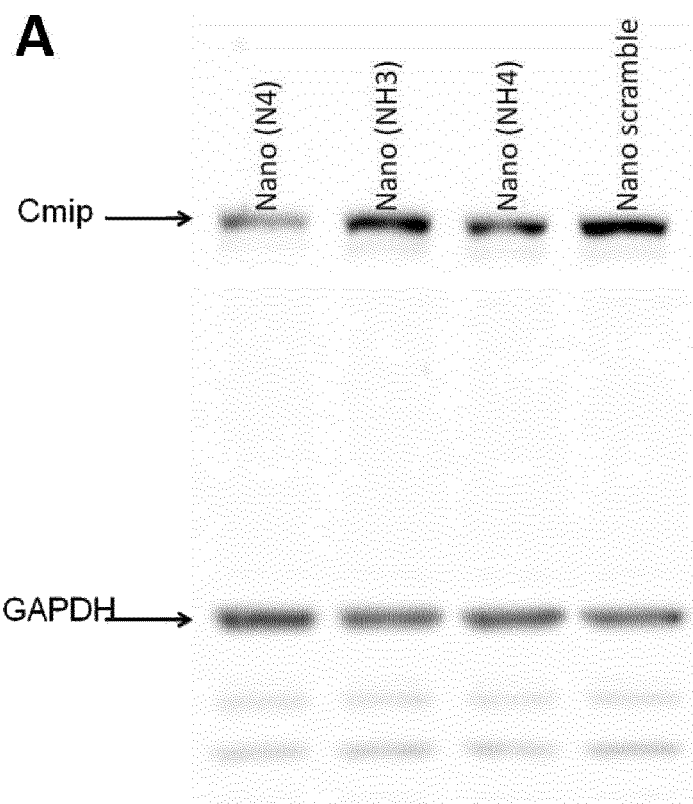
Figure 6:
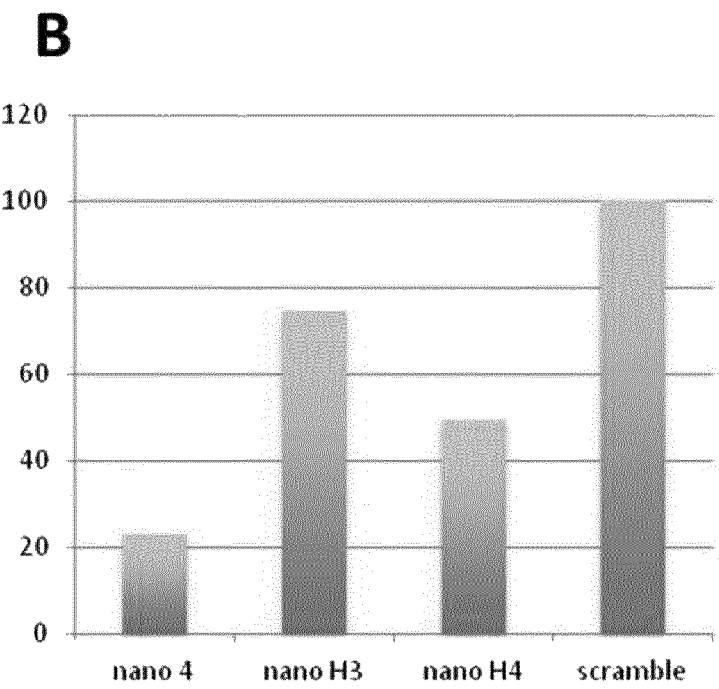

FIG. 6. Nanoparticles comprising anti Cmip sequences [(G6G8) X3=Nano(NH3); (G6G8) X4=Nano(NH4); (G6G8)=Nano(N4)] were tested in culture with HEK cells transfected with a mouse Cmip expression vector. Western Blot with Cmip and GAPDH (A). Quantification of Cmip expression (B)

Figure 7:
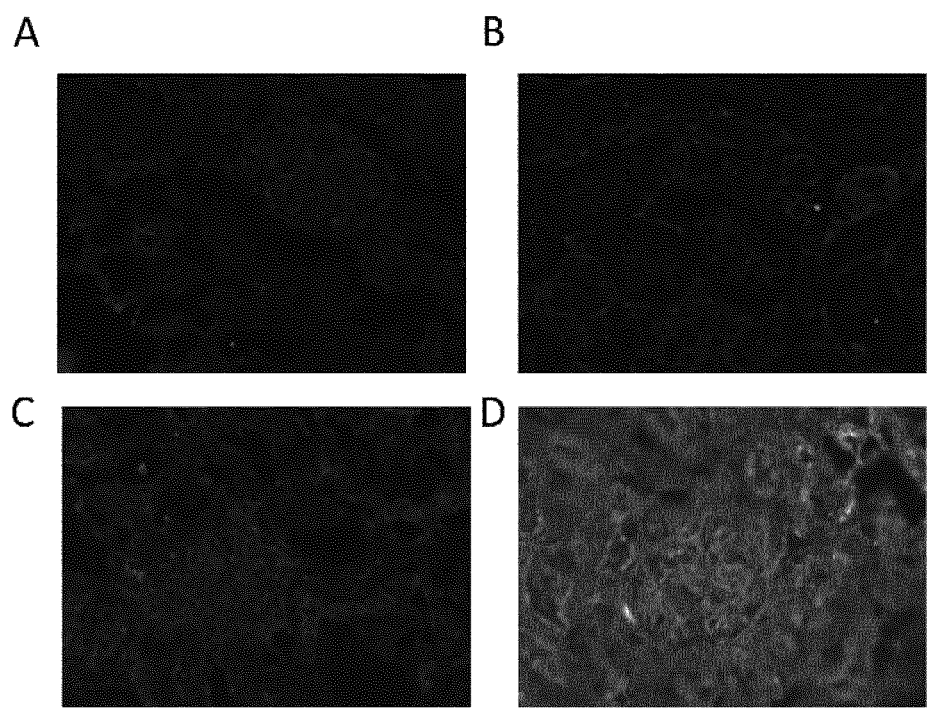

FIG. 7. Kidney sections observed under the fluorescence microscope (×40) with detection of eGFP expression. Control kidney without nanoparticles (A). Mouse kidney 24 h after a retro-orbital injection of 100 microliters of nanoparticles (G6G8) (B). Mouse kidney 48 h after a retro-orbital injection of 100 microliters of nanoparticles (G6G8) (C). Mouse kidney 24 h after a retro-orbital injection of 100 microliters of nanoparticles (G6G8). The injection of nanoparticle was carried out 6 h after induction of proteinuria by LPS (G=glomerulus) (D).

Figure 8:
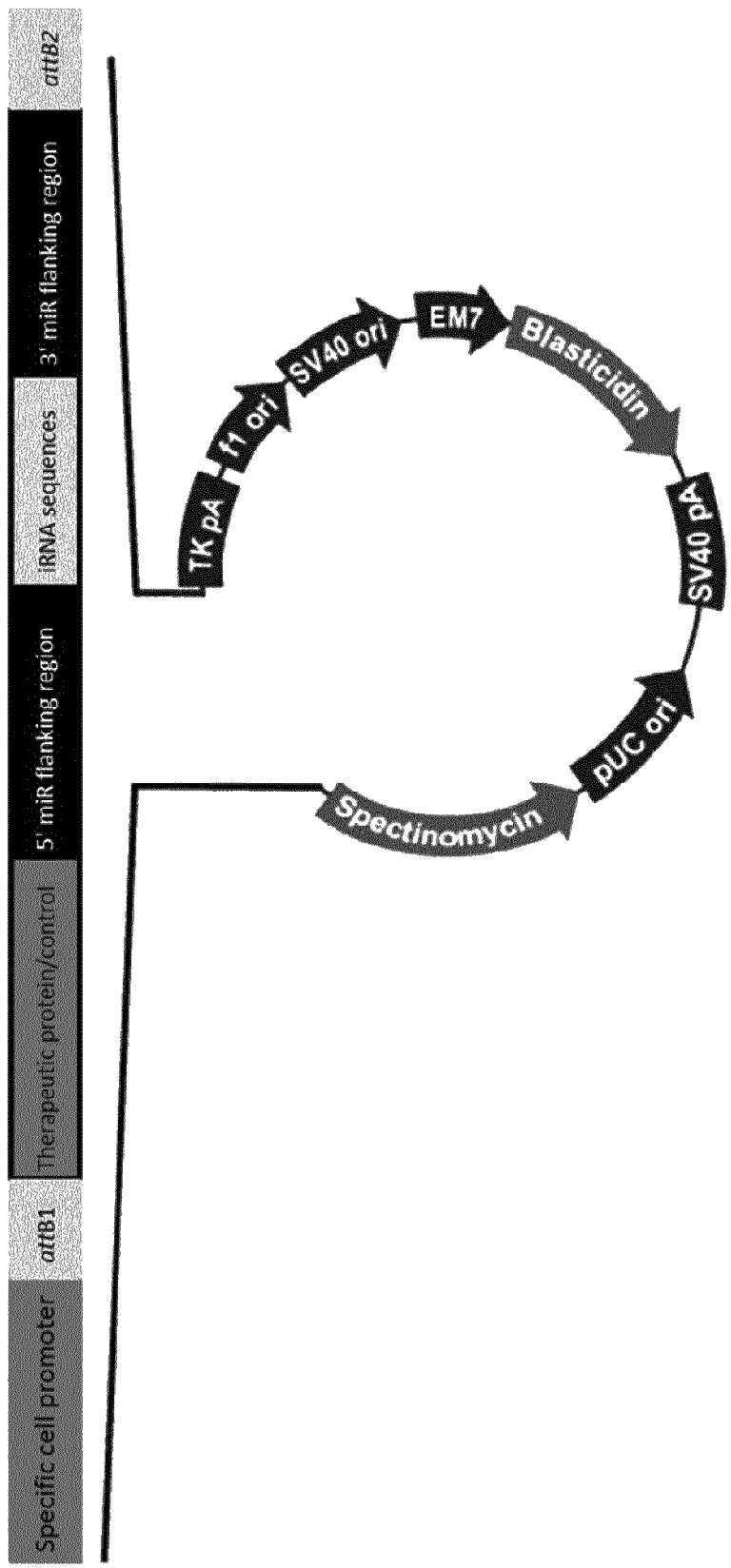

FIG. 8. Expression Vector map.

DETAILED DESCRIPTION OF THE INVENTION

The inventors herein show that nanoparticles with nanoparticle cores and multilayer shells composed of at least one alternate bilayer of one positively charged layer comprising or made of at least one chitosan derivative and one negatively charged layer comprising or made of at least one non-viral expression DNA vector and a last positively charged layer comprising or made of at least one chitosan derivative may be a useful tool to introduce into a cell non-viral DNA vectors which express a protein of interest and/or interfering RNA capable of silencing a target protein in a controlled and tunable manner. It provides more specifically a powerful tool for the treatment of podocyte diseases where CMIP is overexpressed.

Accordingly, in a first aspect it is herein disclosed a nanoparticle comprising nanoparticle core and multilayered shell, wherein:

said multilayer shell is composed of at least one alternate bilayer of one positively charged layer comprising at least one chitosan derivative and one negatively charged layer comprising or consisting of at least one non-viral expression DNA vector, where the outer layer of said multilayer shell is a positively charged layer comprising said at least one chitosan derivative, and said chitosan derivatives are thiolated chitosan derivatives or a mixture of thiolated chitosan derivatives and non thiolated chitosan derivatives.

More precisely, the invention deals with a nanoparticle comprising a nanoparticle core and a multilayered shell, wherein:

said multilayer shell is composed of at least one alternate bilayer consisting of one positively charged layer comprising at least one chitosan derivative, and one negatively charged layer consisting of at least one non-viral expression DNA vector, and one last positively charged layer comprising at least one chitosan derivative coated to the said at least one alternate bilayer (thus, the outer layer of said multilayer shell is a positively charged layer comprising said at least one chitosan derivative), and said chitosan derivatives are thiolated chitosan derivatives or a mixture of thiolated chitosan derivatives and non thiolated chitosan derivatives.

Nanoparticles of the invention or pharmaceutical compositions comprising the same can be for use in the treatment of disorders or diseases by gene therapy.

Gene therapy is defined as the procedure used to treat or improve the health condition of the patient by modifying the patient's cells genetically. It provides an approach to treat both inherited and acquired diseases by delivering a therapeutic gene material and its associated regulatory elements into the nucleus; in order to correct the loss of function caused by mutation or to express a deficient gene product at physiologic levels or to prevent overexpression of a deleterious gene. Accordingly, and more specifically, the non-viral expression DNA vector comprises at least one selected nucleotide sequence of interest; where the said at least one selected nucleotide sequence of interest is more particularly able to correct the loss of function caused by mutation or to express a deficient gene product at physiologic levels or to prevent overexpression of a deleterious gene.

As used herein, the term "about" will be understood by a person of ordinary skill in the art and will vary to some extent on the context in which it is used. If there are uses of the term which are not clear to persons of ordinary skill in the art given the context in which it is used, "about" will mean up to plus or minus 10% of the particular term.

According to the invention, the term "comprise(s)" or "comprising" (and other comparable terms, e.g., "containing," and "including") is "open-ended" and can be generally interpreted such that all of the specifically mentioned features and any optional, additional and unspecified features are included. According to specific embodiments, it can also be interpreted as the phrase "consisting essentially of" where the specified features and any optional, additional and unspecified features that do not materially affect the basic and novel characteristic(s) of the claimed invention are included or the phrase "consisting of" where only the specified features are included, unless otherwise stated. By using the term "consisting essentially of", the drafter signals that the invention necessarily includes the listed ingredients and is open to unlisted ingredients that do not materially affect the basic and novel properties of the invention. A "consisting essentially of" claim occupies a middle ground between closed claims that are written in a "consisting of" format and fully open claims that are drafted in a "comprising" format.

Nanoparticle Core

The nanoparticle core of the invention can be hollow or comprises or consists of at least one organic or inorganic material.

More specifically, the nanoparticle core is hollow or comprises or consists of a material selected from the group consisting of active ingredients, metals; metal-coated materials; metal oxides (such as $Fe_2O_3$); plastics; ceramics; silicon; glasses; mica; graphite; hydrogels; polymers and combinations thereof, preferably gold, silver, platinum, and aluminum and combinations thereof, more preferably gold.

When the nanoparticle core comprises at least one active ingredient, said active ingredient can be a biologically active ingredient, which can for instance potentiate the at least non-viral expression DNA vector or potentiate the treatment triggered by the used DNA vector.

When the nanoparticle core is a material selected from the group consisting of metals; metal-coated materials; metal oxides; plastics; ceramics; silicon; glasses; mica; graphite; hydrogels; polymers and combinations thereof, preferably gold, silver, platinum, and aluminum and combinations thereof, more preferably gold, said nanoparticle core is generally the substrate used as a template to prepare the nanoparticles of the invention, as described below. As it is detailed below, said template can be (pre)treated to have reactive groups, such as thiol and/or sulfonate groups, on its surface as to improve thereafter anchoring of the first layer, for example a thiolated chitosan derivative. The pre-treatment of the template with thiol or sulfonate derivatives, such as with mercapto-(C1-C4)alkyl or aryl sulfonic acid, allows to prepare templates having thiol or sulfonate groups on their surfaces.

When the nanoparticle of the invention comprises a nanoparticle core that is hollow, said nanoparticle are expected to be more flexible and could therefore improve delivery of nucleotide sequences of interest comprised therein.

Chitosan Derivatives

According to the invention, the chitosan derivatives of the positively charged layer(s) in the multilayered shell are thiolated chitosan derivatives only or a mixture of thiolated chitosan derivatives and non thiolated chitosan derivatives. Otherwise specified, when the chitosan derivatives of the positively charged layer(s) in the multilayered film are a mixture of thiolated chitosan derivatives and non thiolated chitosan derivatives, the multilayer shell can be made of at least one layer with thiolated chitosan and another layer made of non thiolated chitosan, and/or can be made of at least one layer of a mixture of thiolated chitosan derivatives and non thiolated chitosan derivatives. The mixture can thus be within the same layer or correspond to alternate layers.

Chitosan derivatives include chitosan. They are polycationic copolymers of glucosamine and N-actetylglucosamine units. On average, the molecular weight of commercially available chitosan derivative is up to 100 kDaltons or preferably between 3800 and 40,000 (or between 3800 and 20,000) Daltons. Chitosan derivatives also include oligomeric derivatives of 3-6 kDa.

A common method for the synthesis of chitosan derivative is the deacetylation of chitin using sodium hydroxide in excess as a reagent and water as a solvent. The degree of deacetylation (% DD) can be determined by NMR spectroscopy, and the % DD in commercial chitosans ranges from 60 to 100%, more particularly from 75% to 100%. The polymer is of value since it is biocompatible, biodegradable and relatively non-toxic. Chitosan and its derivatives include more specifically trimethylchitosan (where the amino group has been trimethylated), mono-N-carboxymethyl chitosan, N-sulfochitosan or chitosan-EDTA conjugates.

According to the present invention, the chitosan derivatives can be thiolated chitosan derivatives. Such thiolated chitosan derivatives are chitosan derivatives as defined above with thiol groups. One can cite for instance chitosanthioglycolic acid conjugates, chitosan-cysteine conjugates or chitosan-4-thio-butyl-amidine (chitosan-TBA) conjugates.

According to a particular embodiment, the chitosan derivatives can all be thiolated chitosan derivatives. More specifically, the chitosan derivatives consist of thiolated chitosan derivatives.

According to another embodiment, the chitosan derivatives are a mixture of thiolated chitosan derivatives and non thiolated chitosan derivatives.

The ratio of thiolated chitosan derivatives/non thiolated chitosan derivatives can vary in a large manner depending on the desired rate of disulfide bonds within the multilayered shell.

The thiolated chitosan derivatives can be prepared by reacting chitosan derivatives with iminothiolane or by oxidation reaction of chitosan derivatives followed by reductive amination, as illustrated by the examples. Oxidation reaction of chitosan derivatives can be a periodate oxidation to selectively generate aldehyde moieties to be substituted subsequently by thiol groups or disulfide groups (disulfide linkage can then be reduced to obtain thiol groups or thiol groups can be oxidized to obtain disulfide bonds).

The degree of thiol substitution in thiolated chitosan derivatives, that is the amount of thiol moieties, can easily be tuned. More particularly, said degree of substitution (DS) generally ranges from 0 to 20%. The degree of substitution of a polymer is the (average) number of substituent groups attached per unit. For instance, a 100% substitution means every sugar unit on a chitosan chain carries a thiol group. A non thiolated chitosan derivative corresponds to a chitosan derivative with 0% DS.

Non-Viral Expression DNA Vector

The function of the vector is to deliver a therapeutic gene to the patient target cell. The vector implemented herein is a non-viral expression DNA vector which refers to a deoxyribonucleic acid (DNA) capable of transporting at least one other nucleotide DNA sequence (hereinafter referred as "nucleotide sequence of interest"), which it has been linked. The non-viral expression DNA vector can be a plasmid or any naked DNA of interest. One type of such vector is a plasmid which refers more specifically to a circular double stranded DNA loop into which additional DNA segments are ligated.

Accordingly, the non-viral expression DNA vector consists essentially of deoxyribonucleic acid molecules.

The plasmid is preferably selected from mammal expression vectors containing a cell specific promoter, a suitable selection gene and a polylinker.

More specifically, the non-viral expression DNA vector comprises at least one selected nucleotide sequence of interest. Said nucleotide of interest is more particularly able to correct the loss of function caused by mutation or to express a deficient gene product at physiologic levels or to prevent overexpression of a deleterious gene. Said nucleotide of interest can be capable of down-regulating the expression of a targeted protein, preferably the nucleotide of interest is a DNA sequence encoding an antisense agent or RNA interference (e.g. microRNA, small interfering RNA, or short hairpin RNA), and/or capable of providing a therapeutic gene expressing a deficient gene product into cells.

The non-viral DNA vectors comprise nucleotides of interest, which preferably express at least one protein of interest and/or at least one interfering RNA capable of silencing a target protein.

The nucleotide of interest can be a DNA sequence encoding at least one protein of interest, such as a therapeutic protein or a control protein. The nucleotide of interest can be a DNA sequence encoding a RNA interference (iRNA) capable of down-regulating the expression of a target protein.

According to a particular embodiment, the non-viral DNA vectors comprise nucleotides of interest, which preferably express two or more interfering RNAs capable of silencing a target protein.

As used herein, the term "iRNA", "RNAi" or "interfering RNA" means any RNA which is capable of down-regulating or silencing the expression of the targeted protein. It encompasses small interfering RNA (siRNA), double-stranded RNA (dsRNA), single-stranded RNA (ssRNA), microRNAs or short hairpin RNA (shRNA) molecules. siRNA or shRNA are usually designed against a region 19-50 nucleotides downstream the translation initiator codon, whereas 5'UTR (untranslated region) and 3'UTR are usually avoided. The chosen siRNA or shRNA target sequence should be subjected to a BLAST search against EST database to ensure that the only desired gene is targeted. Various products are commercially available to aid in the preparation and use of iRNA, such as siRNA or shRNA.

Expression vectors useful in the present invention generally include one or more regulatory sequences and/or flanking regions, selected on the basis of the host cells to be used for expression, which is (are) operatively linked to the nucleic acid sequence(s) to be expressed. Within a recombinant expression vector, "operably linked" is intended to mean that the nucleotide sequence of interest is linked to the regulatory sequence(s) in a manner which allows for expression of the nucleotide sequence(s) in the host cell. The term "regulatory sequence" is intended to include promoters, enhancers, and other expression control elements (e.g., polyadenylation signals). Such regulatory sequences are known in the art and described, for example, in Goeddel (1990) Methods Enzymol. 185:3-7 or Trends Genet. 2016 December; 32(12):801-814. doi: 10.1016/j.tig.2016.10.003. Epub 2016 Nov. 2. Regulatory Enhancer-Core-Promoter Communication via Transcription Factors and Cofactors, Zabidi MA1, Stark A2. Regulatory sequences include those which direct constitutive expressions of a nucleotide sequence in many types of host cells and those which direct expressions of the nucleotide sequence only in certain host cells (e.g., tissue-specific regulatory sequences, such as kidney cells), more preferably podocytes. It will be appreciated by those skilled in the art that the design of the expression vector can depend on such factors as the choice of the cell to be transfected, the level of expression of protein or RNA desired, and the like. The promoter may be an ubiquitous or tissue-specific promoter, in particular a kidney specific promoter. More particularly the promoter is specific to podocytes (Nephrin (NPHS1) or podocin (NPHS2) for example) or lymphocytes (CD4 or Lck for example). Representative ubiquitous promoters include, but are not limited to, the cytomegalovirus enhancer/chicken beta actin (CAG) promoter, the cytomegalovirus enhancer/promoter (CMV), the PGK promoter, the SV40 early promoter, or Rosa26 promoter.

As well, the present invention encompasses the delivery of nucleic acids that provide the polynucleotide as an antisense agent or RNA interference (RNAi) agent (Fire et al. Nature 391:806-811, 1998). Antisense therapy is meant to include, e.g., administration or in situ provision of single- or double-stranded oligonucleotides or their derivatives which specifically hybridize, e.g., bind, under cellular conditions, with cellular mRNA and/or genomic DNA, or mutants thereof, so as to inhibit expression of the encoded protein, e.g., by inhibiting transcription and/or translation (Crooke "Molecular Mechanisms of Action of Antisense Drugs" Biochim. Biophys. Acta 1489(1):31-44, 1999; Crooke "Evaluating the Mechanism of Action of Antiproliferative Antisense Drugs" Antisense Nucleic Acid Drug Dev. 10(2): 123-126, discussion 127, 2000; Methods in Enzymology volumes 313-314, 1999). The binding may be by conventional base pair complementarity, or, for example, in the case of binding to DNA duplexes, through specific interactions in the major groove of the double helix (i.e., triple helix formation) (Chan et al. J. Mol. Med. 75(4):267-282, 1997).

According to an embodiment, the target cells are podocytes.

According to an embodiment, the DNA expression vectors further comprise a promoter specific of a target cell, preferably podocyte (Podocin(NPHS2) or Nephrin (NPHS 1)

According to this embodiment, the nucleotide of interest is capable of down-regulating the expression of CMIP, as defined above (e.g. iRNAs). Some iRNAs capable of down-regulating the expression of CMIP are commercially available. One can cite, for example, but not limited to: InVitrogen, Santa Cruz Biotechnology, Dharmacon. The nucleotide specifically interfering with CMIP more preferably comprises or consists of a sequence selected from the group consisting of:

Sequence ID no 1 (G6)
TGCTGTGAGGATCTTGCTGAGAAAGGGTTTTGGCCACTGACTGACCCTTT

CTCCAAGATCCTCA;

Sequence ID no 2 (G8)
TGCTGTGTTGATGAACTCTTCATAGCGTTTTGGCCACTGACTGACGCTAT

GAAGTTCATCAACA.

According to another embodiment, the DNA expression vectors comprise nucleotides of interest that express at least one, or preferably two or more different, interfering RNA capable of silencing a target protein. As detailed in the examples, the association of two or more different silencing sequences for the same target protein is more efficient than a single interfering RNA sequence.

According to a specific embodiment, when the target protein is CMIP, the DNA expression vectors comprise nucleotides comprising or consisting in SEQ ID n°1, SEQ ID n°2 and preferably both SEQ ID n°1 and SEQ ID n°2.

According to another embodiment, the DNA expression vectors comprise nucleotides of interest that express at least one (or two or more) interfering RNA capable of silencing a mutated protein and express a corresponding functional protein which is encoded by a sequence to which said interfering RNAs do not bind.

According to specific embodiments, the mutated protein can be a protein of kidney slit diaphragm, preferably nephrin, podocine, or CD2AP.

Multilayer Shells

The multilayer shell comprises at least one alternate bilayer of one positively charged layer comprising at least one chitosan derivative as defined above and one negatively charged layer comprising or consisting of at least one non-viral expression DNA vector as defined above. The assembly is based on electrostatic interactions between positively and negatively charged polymers. The number of bilayers can vary from one to 2, 3, 4, 5, 6, 7, 8, 9, or more in the multilayer shell.

According to a specific embodiment, the multilayer shell comprises at least one alternate bilayer of one positively charged layer comprising at least one chitosan derivative as defined above and one negatively charged layer comprising or consisting of at least one non-viral expression DNA vector as defined above coated to the template, and a last one positively charged layer comprising at least one chitosan derivative coated to the said at least one alternate bilayer as defined above. This last positively charged layer comprising at least one chitosan derivative is the outermost layer of the nanoparticle.

According to specific embodiments, the first bilayer which is in direct contact with the core of the nanoparticle, i.e., the innermost bilayer, is composed of one positively charged layer comprising at least one chitosan derivative which is in direct contact with the core of the nanoparticle, and one negatively charged layer comprising or consisting of at least one non-viral expression DNA vector. Accordingly, one last positively charged layer comprising at least one chitosan derivative is added, which is in direct contact with the last layer of the last alternative bilayer. Thus, the outermost layer of the nanoparticle is constituted of a positively charged layer comprising at least one chitosan derivative.

According to an alternative embodiment, the first bilayer which is in direct contact with the core of the nanoparticle, i.e., the innermost bilayer, is composed of one negatively charged layer comprising or consisting of at least one non-viral expression DNA vector which is in direct contact with the core of the nanoparticle, and one positively charged layer comprising at least one chitosan derivative.

Thus, the outermost layer of said multilayer shell is a positively charged layer comprising said at least one chitosan derivative (no need to add a positively charged layer).

According to an alternative embodiment, an outer neutral layer can be added on the last positively charged layer comprising said at least one chitosan derivative as defined above. A neutral outermost layer can be considered depending on the target tissue or cells (for instance circulating cells).

According to another embodiment or in addition to the embodiments as defined above, the outer layer of the shell can be modified, for instance with grafted antibodies, as to increase selectivity of the target tissue or cells. One of ordinary skill in the art is able to select specific antibodies to target specific tissue or cells.

The number of alternate bilayers of the multilayer shell can vary in a large extent depending on the desired effect. For instance, it may vary from 1 to 20 bilayers, preferably from 1 to 15, more preferably from 1 to 10 bilayers.

According to a specific embodiment, the multilayer shell is composed of one positively charged layer comprising at least one chitosan derivative, that is preferably in direct contact with the core of the nanoparticle, one negatively charged layer comprising or consisting of at least one non-viral expression DNA vector, both layers corresponding to the first alternate bilayer coated to the template, and an outer layer which is a positively charged layer comprising at least one chitosan derivative.

According to another specific embodiment, the multilayer shell is composed of one positively charged layer comprising at least one chitosan derivative, that is preferably in direct contact with the core of the nanoparticle, one negatively charged layer comprising or consisting of at least one non-viral expression DNA vector, both layers corresponding to the first alternate bilayer coated to the template, and an outer layer which is a positively charged layer comprising at least one chitosan derivative, and additional alternate bilayers (1, 2, 3, 4, 5, 6, 7, 8, 9, or more) are comprised in the multilayer shell, between the first bilayer and the outer layer. The additional alternate bilayers can either be of the same natures as the positively and/or negatively charged layers as defined above or can be of different types positively and/or negatively charged layers (as described below).

As mentioned before, nanoparticles that are fabricated by layer-by-layer deposition of non-viral expression DNA vector and specific polycation, i.e., thiolated chitosan derivatives, allow the vector to be directly and locally-delivered to the target cell upon degradation or physical erosion of the polycation, in a controlled and tunable manner.

Nanoparticle and Compositions

The mean size (mean diameter) of the nanoparticles of the invention may also vary in a large extent, and depends on the size of the implemented core used as a substrate (also called template) to prepare the particles of the invention and also depends on the size (i.e. thickness) of the multilayer shell. Said size is controlled by the layer-by-layer deposition method so that standard deviation of size of the nanoparticles is very low.

Generally, the mean size of the nanoparticles of the invention is from 10 nm or from 20 nm to 1 μm, more preferably from 20-80 or 40-80 nm, even more preferably from 20-60 nm.

The skilled person knows the right techniques to be used to determine the value of the diameter of the particles according to the invention. For example, the average diameter of the particles in a set of particles, standard deviation and size distribution can be determined, in particular, by statistical studies of microscopy images, for example, those generated by scanning electron microscopy (SEM) or transmission electron microscopy (TEM).

When the particles are part of a set, size (or diameters) values as specified above may correspond to the average diameter of all particles, even if some of the particles in the set have diameters outside this range. Advantageously, all particles in the set have a diameter as defined above.

In one embodiment, the standard deviation of particle sizes in any set of particles produced according to the invention is less than or equal to 20%, preferably less than or equal to 15%.

Another aspect of the invention is a composition comprising nanoparticles of the invention as described herein and more particularly a pharmaceutical composition comprising the same with a pharmaceutically acceptable carrier.

In a specific embodiment, the term "pharmaceutically acceptable" means approved by a regulatory agency of the Federal or a state government or listed in the U.S. or European Pharmacopeia or other generally recognized pharmacopeia for use in animals, and humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, sodium stearate, glycerol monostearate, talc, sodium chloride, dried skim milk, glycerol, propylene glycol, water, ethanol and the like.

The composition, if desired, can also contain minor amounts of wetting or emulsifying agents, or pH buffering agents. These compositions can take the form of solutions, suspensions, emulsions, tablets, pills, capsules, powders, sustained-release formulations and the like. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the therapeutic vectors (more specifically the nucleotide sequences of interest) comprised in the nanoparticles of the invention, together with a suitable amount of carrier so as to provide the form for proper administration to the subject. In a particular embodiment, the nanoparticles of the invention are formulated in a composition comprising phosphate-buffered saline and supplemented with 0.25% human serum albumin. In another particular embodiment, the nanoparticles of the invention are formulated in a composition comprising ringer lactate and a non-ionic surfactant, such as pluronic F68 at a final concentration of 0.01-0.0001%, such as at a concentration of 0.001%, by weight of the total composition. The formulation may further comprise serum albumin, in particular human serum albumin, such as human serum albumin at 0.25%. Other appropriate formulations for either storage or administration are known in the art, in particular from WO 2005/118792 or Allay et al., 2011.

In a preferred embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lignocaine to, ease pain at the, site of the injection.

Preparation of Nanoparticles

The method for the preparation of nanoparticles of the invention, generally comprises the following steps consisting of:

a. providing a core nanoparticle that comprises or consists of a material selected from the group consisting of metals, metal-coated materials, metal oxides, plastics, ceramics, silicon, glasses, mica, graphite, hydrogels, polymers and combinations thereof, preferably the material is gold, b. at least one step of layer-by-layer depositing alternatively a positively charged layer comprising at least one chitosan derivative and a negatively charged layer comprising at least one non-viral expression DNA vector, on the surface of the core of step (a) to provide a polyelectrolyte assembly coating on the surface of the core, where the last deposited layer is a positively charged layer comprising said at least one chitosan derivative, where the chitosan derivatives of the polyelectrolyte assembly are thiolated chitosan derivatives or are a mixture of thiolated chitosan derivatives and non thiolated chitosan derivatives, c. optionally, removal of the material of step (a).

More specifically, the method for the preparation of nanoparticles of the invention, generally comprises the following steps consisting of:

a. providing a core nanoparticle that comprises or consists of a material selected from the group consisting of metals, metal-coated materials, metal oxides, plastics, ceramics, silicon, glasses, mica, graphite, hydrogels, polymers and combinations thereof, preferably the material is gold,
b. a step providing a first alternate bilayer consisting of one positively charged layer comprising at least one chitosan derivative coated to the core nanoparticle and one negatively charged layer comprising or consisting of at least one non-viral expression DNA vector, and optionally at least one additional step providing an alternate bilayer consisting of one positively charged layer comprising at least one chitosan derivative coated to the first or previously deposited bilayer and one negatively charged layer comprising or consisting of at least one non-viral expression DNA vector, and
c. adding a last positively charged layer comprising at least one chitosan derivative, coated to the last deposited bilayer of step (b) to provide a polyelectrolyte assembly, where the last deposited layer is a positively charged layer comprising said at least one chitosan derivative,
d. optionally, removal of the material of step (a).

The nanoparticle core provided by step (a), used as a substrate, consists of a material selected from the group consisting of metals; metal-coated materials; metal oxides; plastics; ceramics; silicon; glasses; mica; graphite; hydrogels; polymers and combinations thereof, preferably gold, silver, platinum, and aluminum and combinations thereof, more preferably gold.

As used herein, "nanoparticle core" refers to any particle having a size from about 20 nm to about 1 μm. The diameter of the nanoparticle core as described herein can range in the size from about 20 nm to 1 μm, preferably from about 40 nm to 80 nm.

In various embodiments, the nanoparticle core is essentially spherical.

In certain embodiments, the core may be negatively charged to facilitate the coating with a first positively charged polymer layer. In other embodiments, the core may be positively charged such that coating with a negatively charged first layer is facilitated. In still other embodiments, the surface of the core may have reactive groups, such as thiol and/or sulfonate groups, to be used as an anchoring layer. Accordingly, said core can be previously treated to be negatively or positively charged and/or have reactive groups, such as thiol and/or sulfonate groups, on its surface as to improve thereafter anchoring of layers.

The preferred manufacturing method for the polyelectrolyte assemblies identified as step (b) above) comprises at least one step of layer-by-layer depositing and is illustrated by the examples section below. In general, films may be fabricated from chitosan derivatives, as polycations, and non-viral expression DNA vectors, as polyanions, using any of the generally accepted methods known to those of skill in the art including, but not limited to, dip coating, spray coating, brush coating, roll coating, spin casting, or combinations thereof. In one particularly useful method, the provided material may be coated using a manual or automated dipping protocol similar to those reported previously for polycation/DNA systems (Jewell C M, Zhang J, Fredin N J, Lynn D M, Multilayered polyelectrolyte films promote the direct and localized delivery of DNA to cells, J Control Release, 2005 Aug. 18; 106(1-2):214-23, and J. Zhang, L. S. Chua, D. M. Lynn, Multilayered Thin Films that Sustain the Release of Functional DNA Under Physiological Conditions. Langmuir 2004, 20, 8015-8021). Generally: 1) A substrate used (if negatively charged) as a template is submerged in a solution of polycations comprising chitosan derivative for a period of time suitable to allow sufficient adsorption of said polycations to the substrate. It deserves noting that thiol and/or other reactive groups can be attached previously to the substrate to be used as an anchoring layer (see ACS Appl. Mater. Interfaces 2016, 8, 5586-5594), 2) the substrate is removed and immersed in one or several wash baths (e.g. buffer solutions), 3) the substrate is submerged in a solution of polyanions comprising non-viral expression DNA vectors for a period of time suitable for the adsorption of said vectors, and 4) the substrate is again washed or rinsed in the manner described above for step 2. Steps 1) and 3) can be interchanged, i.e. if the used substrate is positively charged, the substrate is first submerged in a solution of polyanions comprising non-viral expression DNA vectors and then submerged in a solution of polycations comprising chitosan derivatives. This cycle is generally repeated until the desired numbers of layers have been deposited or the desired thickness of the deposited assembly has been reached. The layering can be verified using zeta potential measurements of the particles following deposition of each layer.

As mentioned before, the last deposited layer is preferably a positively charged layer comprising at least one chitosan derivative, as to prevent vectors from degradation, reduce the immune reaction against naked DNA, promote the interaction and crossing of negatively charged membranes, such as kidney barrier.

According to an alternative embodiment, an outer neutral layer can be added on the bilayer and more precisely on the last positively charged layer. Thus, the outermost layer is neutral in this alternative embodiment. A neutral outermost layer can be considered depending on the target tissue or cells (for instance, circulating cells or tissue with no basal membrane).

According to another embodiment or in addition to the embodiments as identified above, the outermost layer of the shell can be modified, for instance with grafted antibodies, as to increase selectivity of the target tissue or cells. One of ordinary skill in the art is able to select specific antibodies to target specific tissue or cells.

According to a particular embodiment, the method for the preparation of nanoparticles of the invention relates to a method where the first step of (b) is a step of depositing a positively charged layer comprising at least one chitosan derivative (or respectively a negatively charged layer comprising at least one non-viral expression DNA vector on the surface of the core of step (a), to provide a first layer coating comprising said at least one chitosan derivative (or respectively a first layer comprising at least one non-viral expression DNA vector) on the surface of the core, followed by a step of depositing a negatively charged layer comprising at least one non-viral expression DNA vector (or respectively a positively charged layer comprising at least one chitosan derivative), optionally said two steps can be reiterated alternatively, and where preferably the last deposited layer is a positively charged layer comprising said at least one chitosan derivative.

As mentioned before, the chitosan derivatives implemented in the method according to the invention are thiolated chitosan derivatives or a mixture of thiolated chitosan derivatives and non thiolated chitosan derivatives.

According to a particular embodiment, the chitosan derivatives can all be thiolated chitosan derivatives. More specifically, the chitosan derivatives are thiolated chitosan derivatives.

According to another embodiment, the chitosan derivatives are a mixture of thiolated chitosan derivatives and non thiolated chitosan derivatives, as defined before.

According to a specific embodiment, the first step of (b) is a step of depositing a positively charged layer comprising at least one chitosan derivative, where said chitosan derivative comprises or consists of thiolated chitosan derivatives. In that context, the thiol groups of said thiolated chitosan derivatives can adhere to the surface of the core and can therefore be used as an anchoring layer.

The thiolated chitosan derivatives used in the present method are previously prepared by reacting chitosan derivatives with iminothiolane or by oxidation reaction of chitosan followed by reductive amination.

The term "polyelectrolyte assembly" or "polyelectrolyte assembly coating", as used herein, shall refer to films having at least one "bilayer" of deposited material. The term "bilayer", as used herein, shall refer to the accumulated layers of material deposited on a surface as a result of having passed through at least one complete cycle of the general steps 1-4 as identified above. Preferred embodiments utilize films having at least one or two bilayers of a positively charged layer comprising at least one chitosan derivative and a negatively charged layer comprising at least one non-viral expression DNA vector, alternatively. More preferred embodiments utilize films having at least three or four bilayers of positively charged layer comprising at least one chitosan derivative and a negatively charged layer comprising at least one non-viral expression DNA vector, alternatively. In certain embodiments, at least two of the nucleic acid layers include nucleic acids characterized by differing nucleotide sequences of interest. The sequential delivery of differing nucleic acids to a cell is therefore contemplated by the present invention. In other embodiments, one or more (or possibly all) negatively charged layers comprise(s) the same or different non-viral expression DNA vectors characterized by two or more differing nucleotide sequences of interest. The delivery of several differing nucleotide sequences of interest to a cell is therefore contemplated by the present invention. The DNA expression vectors can for instance express thereby at least one interfering RNA capable of silencing a mutated protein and also express a corresponding functional protein which is encoded by a sequence to which said interfering RNAs do not bind.

Layer-by-layer deposition, also termed LBL fabrication, offers an opportunity to design films containing spatially segregated regions of polyelectrolyte confined to different regions of a film (e.g., in either the top or the bottom). It is therefore possible to use the layered nature of these films to prepare assemblies that release different vectors or different concentrations thereof or to control the kinetics with which two differing nucleotide sequences of interest are released by incorporating positively charged layers comprising at least one chitosan derivative that erode more or less slowly depending on the compositions (e.g. chemical natures) of positively charged layers or concentrations thereof.

In certain embodiments, the composition of the layers and methods for preparing the same can be fine-tuned to adjust the degradation rate of each layer within the film. For instance, to adjust the degradation rate of each layer within the film, the positively charged layer(s) and/or the negatively charged layer(s) as described above can further comprise additional polymers and/or polyelectrolytes, or the multilayer shell (or the polyelectrolyte assembly) can comprise additional layers made of polymers and/or polyelectrolytes (different from chitosan derivatives and/or non-viral expression DNA vectors). For example, the degradation rate of the layers can be decreased by associating hydrophobic polymers such as hydrocarbons and lipids with one or more of the layers. Alternatively, the polyelectrolyte layers may be rendered more hydrophilic to increase their hydrolytic degradation rate. In certain embodiments, the degradation rate of a given layer can be adjusted by including a mixture of polyelectrolytes that degrade at different rates or under different conditions. In other embodiments, the layers may further comprise a mixture of degradable and non-degradable polyelectrolytes. Any non-degradable polyelectrolyte can be used with the present invention. Exemplary non-degradable polyelectrolytes that could be used in thin films of the present invention include poly(styrene sulfonate) (PSS), poly(acrylic acid) (PAA), linear poly(ethylene imine) (PEI), poly(diallyldimethyl ammonium chloride) (PDAC), and poly(allylamine hydrochloride) (PAH).

Alternatively or additionally, the degradation rate may be fine-tuned by associating or mixing non-biodegradable, yet biocompatible polymers (polyionic or non-polyionic) with one or more of the layers. Suitable non-biodegradable, yet biocompatible polymers are well known in the art and include polystyrenes, certain polyesters, non-biodegradable polyurethanes, polyureas, poly(ethylene vinyl acetate), polypropylene, polymethacrylate, polyethylene, polycarbonates, and poly(ethylene oxide)s.

Furthermore, thanks to the layer-by-layer process, the composition of individual layers may be varied to tailor the degradation rate of various portions of the film. For example, the upper layers of the film, closer to the surface (including or not the outer layer which is a positively charged layer), may be adjusted to degrade faster than the layers of the film closer to the substrate, or vice versa. Depending on the thickness of the film, the degradation rate within the film may be varied cyclically (e.g., for periodic release). Additionally, or alternatively, the upper layers of the film, closer to the surface, including or not the outer layer, may be adjusted to degrade under a first set of conditions while the layers of the film that are closer to the substrate are adjusted to degrade under a second set of conditions.

Additionally, or alternatively, and as already described above, the composition of layers or methods for preparing the same may be tuned by the ratio of thiolated chitosan derivatives/non thiolated chitosan derivatives of the layers comprising chitosan derivatives.

According to optional step (c), removal of the material of step (a) can be implemented either to obtain a hollow core or to replace the material of step (a) by another material as defined above. By way of example, the material of step (a) can be replaced by at least one active ingredient as defined above.

Step (c) can be carried out by a simple method such as by dissolution of the material used at step (a). For instance, the obtained modified gold nanoparticles are suspended in an aqueous solution of KCN or any other suitable etchant of the template. Gold dissolution occurs via transport of etchant species through the polymer shell to the core, where $Au^0$ is converted to $[Au(CN)_4]^-$. This can be evidenced by a loss of the gold absorbance and/or by the observation of a hollow core, for instance by TEM or by ICP measurements.

The structural integrity of the obtained particles is maintained following gold dissolution. The diameter of the resulting hollow core is in the range of size of the initial particle template.

Any suitable solvent or etchant can be employed to dissolve the nanoparticle core. For example, HF can be used for dissolving silver (Ag) particles and EDTA can be used for dissolving CaCO₃ particles. Typically, the solvent or etchant is chosen based on the nature of the nanoparticle core. The solvent or etchant can be biologically compatible when the nanoparticles are to be used for biological applications.

After step (b), or optionally step (c), the method may comprise a further step consisting of recovery of the prepared nanoparticles. Recovery can be carried out for instance by dialysis method. The recovery step is preferably followed by a washing step.

The Present Invention Also Relates to the Nanoparticles Obtained by the Method as Described Above.

Methods and Uses of the Invention

The present invention further relates to nanoparticles or compositions as described above for use as a medicament.

Nanoparticles or pharmaceutical compositions of the invention are more specifically for use in the treatment of disorders or diseases, more specifically by gene therapy.

Nanoparticles or pharmaceutical compositions of the invention are more specifically for use in the treatment of a podocyte disease (idiopathic nephrotic syndrome or a chronic glomerular disease). Idiopathic nephrotic syndrome (INS) defines two entities, minimal change nephrotic syndrome (MCNS) and focal and segmental glomerulosclerosis (FSGS) that represent 85% of the glomerular nephropathies in children and 25 to 30% in adults.

According to specific embodiments, the nanoparticles for use in the treatment of disorders or diseases, more specifically by gene therapy, preferably comprise DNA expression vectors which express at least one interfering RNA capable of silencing a mutated protein and express a corresponding functional protein which is encoded by a sequence to which said interfering RNAs do not bind.

The mutated protein is a protein that has lost its function. It can be any kind of proteins. More specifically said mutated protein can be a protein of kidney slit diaphragm, preferably nephrin, podocine, or CD2AP.

Nanoparticles or pharmaceutical compositions of the invention are more specifically for use in the treatment of a podocyte disease, wherein the at least one non-viral expression DNA vector encodes at least one interfering RNA capable of silencing CMIP.

The present invention also relates to a method for the treatment of disorders or diseases, more preferably by gene therapy, wherein nanoparticles or pharmaceutical compositions of the invention are administered to a subject in need of such treatment.

The present invention also relates to a method for the treatment of podocyte disease, wherein nanoparticles or pharmaceutical compositions of the invention are administered to a subject in need of such treatment, and wherein the said at least one non-viral expression DNA vector encodes at least one interfering RNA capable of silencing CMIP.

As used herein, the term "treating" and "treatment" refers to administering to a subject an effective amount of a composition or nanoparticles of the invention so that the subject has a reduction in at least one symptom of the disease or an improvement in the disease, for example, beneficial or desired clinical results. For purposes of this invention, beneficial or desired clinical results include, but are not limited to, alleviation of one or more symptoms, diminishment of extent of disease, stabilized (i.e., not worsening) state of disease, delay or slowing of disease progression, amelioration or palliation of the disease state, and remission (whether partial or total), whether detectable or undetectable. Treating can refer to prolonging survival as compared to expected survival if not receiving treatment. Alternatively, treatment is "effective" if the progression of a disease is reduced or halted. "Treatment" can also mean prolonging survival as compared to expected survival if not receiving treatment. Those in need of treatment include those already diagnosed with a disorder associated with expression of a polynucleotide sequence, as well as those likely to develop such a disorder due to genetic susceptibility or other factors. As used herein, the term "treating" and "treatment" also refers the prevention of a disease or disorder, which means delaying or preventing the onset of such disease or disorder.

The invention further relates to nanoparticles or compositions as described above for use in a method for treating podocyte disease.

The invention further relates to the use of nanoparticles or compositions as described above for the manufacture of a medicament for the treatment of podocyte disease.

The invention further relates to a method for treating podocyte disease, comprising administering to a subject in need thereof an effective amount of nanoparticles or compositions as described above.

The amount of the nanoparticles or compositions of the invention which will be effective in the treatment of podocyte diseases can be determined by standard clinical techniques. In addition, in vivo and/or in vitro assays may optionally be employed to help predict optimal dosage ranges. The precise dose to be employed in the formulation will also depend on the route of administration, and the seriousness of the disease, and should be decided according to the judgment of the practitioner and each patient's circumstances. The dosage of the nanoparticles or compositions administered to the subject in need thereof will vary based on several factors including, without limitation, the route of administration, the subject's age or the level of expression necessary to obtain the required the therapeutic effect. One skilled in the art can readily determine, based on its knowledge in this field, the dosage range required based on these factors and others.

The following examples are, of course, offered for illustrative purposes only, and are not intended to limit the scope of the present invention in any way. Indeed, various modifications of the invention in addition to those shown and described herein will become apparent to those skilled in the art from the foregoing description and the following examples and fall within the scope of the appended claims.

EXAMPLES

Materials and Methods

Design of the CMIP Inhibiting Sequences.

Different available anti-Cmip siRNAs were tested in vitro on Cmip transfected HEK cells. The 2 most efficient sequences were selected and modified to adapt them for cloning into the pCDNA 6.2 vector (Invitrogen)—See FIG. 8. These sequences were added by ligation, alone or together, into the expression vector.

The scramble sequence is as follows:

```
                              Sequence ID no 3 (scramble)
TGCTGAAATGTACTGCGCGTGGAGACGTTTTGGCCACTGACTGACGTCTC

CACGCAGTACA
```

Nanoparticles/Nanocapsules

1. Chitosan Modification (Polycation Modification, i.e. Chitosan Derivative)

1.1. Modification of Chitosan with 2-iminothiolane

To 200 μL of the chitosan solution, 50 mg of 2-iminothiolane and 800 μL of 2% dithiothreitol were added and the reaction was kept for 7 h at 55° C. After the reaction, excess reagents were removed by dialysis process.

1.2. Modification of Chitosan with 2-aminoethanethiol or 2,2'-dithiobis(ethylamine)

Periodate oxidation of chitosan were first performed to selectively generated aldehyde moieties which were substituted to introduce thiol groups. Two methods based on the nucleophilic substitution reaction of the aldehyde groups were investigated to functionalize the chitosan with thiol groups. (i) The first one is a direct method, implying the 2-aminoethanethiol. (ii) The second one is a two-step method, enabling disulfide bridge introduction with the 2,2'-dithiobis(ethylamine). Then, the thiol groups are obtained after disulfide linkage reduction.

2. Surface Modification: Flat Substrate and Nanoparticles

The overall preparation process of (chitosan/DNA derivative) or (chitosan derivative/DNA derivative) bilayered nanocapsules relies on successive steps including pre-treatment of the gold nanoparticles surface, sequential deposition of chitosan and DNA derivative polyelectrolytes and degradation of the gold core as described here-below. The pre-treatment of the gold nanoparticles with thiol derivatives, such as mercapto-(C1-C4)alkyl or aryl sulfonic acid; allowed to prepare gold nanoparticles having thiol and sulfonate groups on their surfaces. Demonstration of the in situ formation of the multilayer assembly films on flat gold surface was monitored by Quartz Crystal Microbalance with Dissipation (QCM-D) technique Surface Modification of Gold Nanoparticles Though Layer-by-Layer Polyelectrolyte Self-Assembly.

100 μL of chitosan solution as prepared above was added to a suspension of pre-treated gold nanoparticles. After 20 min, the polymer excess was removed from the supernatant fraction after centrifugation. This washing process was repeated two more times keeping the final volume equal to 1 ml. This adsorption process was further reproduced with the polyanion through addition of 100 μL of DNA derivative solution as prepared above to a suspension of chitosan-modified gold nanoparticles. This procedure describes the assembly of a single bilayer: (chitosan/DNA derivative) and was repeated until the desired number of assembled bilayers was achieved (chitosan/DNA derivative)$_n$ (n representing the number of bilayer). At last, the process was further reproduced with the deposit of a last layer of chitosan so that the outer layer is a chitosan derivative layer.

Formation of (Chitosan/DNA Derivative)n Based Nanocapsules Through Selective Removal of Gold Template:

Capsules were formed via dissolution of the gold template by treatment with potassium cyanide solution, followed by a dialysis step to remove the gold complex.

Cell Culture and Transfection Assay.

To test the iRNA and the nanoparticles, HEK cells where seeded at 2 million Cells/10 cm plates and transfected with 1 μg mouse Cmip expression vector using Genecellin (BCC) as transfection reagent. One hour after transfection the culture medium was replaced with fresh medium containing the nanoparticles as described previously. 24 h after a total protein extract was prepared and used for western blot preparation.

Western Blot Preparation

20 μg of cell lysate were submitted to acrylamide gel electrophoresis and transferred to a PVDF membrane. The membrane was probed successively with anti-eGFP, anti-Cmip and anti-GAPDH antibodies. The signal was revealed using an HRP conjugated secondary antibody. The signal was recorded with the Fusion-SL camera system (Vilber Lourmat, France) and quantified using the ImageJ.

In Vivo Experiments

The mice were injected with LPS (10 μg/g) or PBS by intraperitoneal injection (IP). Five to six hours later they were anaesthetized (Ketamine/Xylazine) and a retro-orbital injection of 100 μl of nanoparticles solution (5·10$^9$/ml) as prepared above was administered. 24 h or 48 h after the LPS injection, the mice were killed and the kidneys were prepared for immunofluorescence detection.

All experiments involving animals were conducted in accordance with French laws.

Results

To establish the method, stepwise adsorption of chitosan and DNA derivative is first monitored in real time by in situ QCM-D experiments on flat surface mainly to study the adsorption kinetics. For this, a modified quartz substrate is immersed in the solvent and after an equilibrium time of a few minutes, the different polyelectrolyte is added in the measuring cell. It is worth noting that the surface was flushed with the buffer between each polyelectrolyte solution. The typical decrease of the frequency signal by further increasing the number of adsorption cycles was observed indicating that mass was being added onto the substrates surface (FIG. 1). As soon as the quartz surface is rinsed with solvent, the frequency shift slightly increases due to the polyelectrolyte excess removal. These results are in agreement with the success of the assembly of chitosan and DNA derivatives.

The charge reversal after each step of polymer deposition is one of the prerequisites for sequential deposition of oppositely charged polyelectrolytes onto surfaces. Zeta potential measurement is the most efficient technique to monitor each stage of the polymer coating (FIG. 2). As expected after the initial (or pre-)treatment with the thiol derivative, the zeta potential value changes from ~−33 mV to ~−20 mV due to the presence of sulfonate groups (provided by thiol derivative containing sulfonate groups) on the surface. After chitosan deposition, the value is ~+40 mV and ~−20 mV after DNA derivative deposition.

FIG. 3 shows transmission electron micrographs (TEM) of bare gold nanoparticles, multilayer-coated gold nanoparticles and hollow capsules, formed after cyanide-mediated core etching of the polyelectrolyte-coated or bilayer-coated (chitosan/DNA derivative)$_n$ (n=1) gold hybrid nanoparticles with the addition of a last layer of chitosan constituting the outermost layer of the nanoparticle. This observation clearly validates forcefully the success of the implemented strategy. Drying effects and the high vacuum conditions inherent to TEM observations induce clumping of neighbouring capsules. No presence of atomic gold was detected by energy dispersive X-ray (EDX) analysis or even by the Inductively Coupled Plasma Optical Emission Spectrometry (ICP-OES) analysis; the absence of residual gold was corroborated to the polymer capsules.

It is thus clearly evidenced that the present multilayer allowed cellular adhesion (HEK cells). Indeed, well-adhered cells were observed on gold flat surfaces previously modified with (chitosan/DNA derivative)$_n$ multilayer and not with the unmodified one (FIG. 4).

The results show that the nanoparticles of the invention are able to penetrate non-treated HEK cells (FIG. 5 lines −Cmip). But in this case the efficiency of cell penetration is less than in the case of cells previously transfected (FIG. 5 lines +Cmip). The effect of genecellin on the cell membrane is certainly the reason of this increase of intracellular nanoparticle detection. The effect of Cmip expression inhibition is dose dependent as showed in FIG. 5 lines (+Cmip). The expression of Cmip is decreased in the line with 150 µl of nanoparticles (line A +Cmip) compared to the line with 50 µl of nanoparticles (line B +Cmip). It is demonstrated that the association of two or more different silencing sequences is more efficient than a single sequence (data not shown) but that the multimerization of the same active silencing sequence did not increase the effect of this sequence but can reduce it, as showed in FIG. 6. For this experiment the sequence (G6G8), (G6G8)X3 (i.e. the sequence G6G8 is present three times in the used vector), (G6G8)X4 (i.e. the sequence G6G8 is present four times in the used vector) and Scramble, respectively Nano (N4), Nano (NH3), Nano (NH4) and Nano (Scramble) were used. As it can be seen, the quantification of Cmip expression is reduced from around 80% with Nano (N4) when the inhibition of Cmip expression is only 25% and 50% respectively with Nano (NH3) and Nano (NH4).

The in vivo experiments on LPS treated or non LPS treated mice. It shows that a low amount of nanoparticles, illustrated by a low eGFP expression signal, may reach the glomerular compartment in control mice without proteinuria (FIGS. 7 B and C). In contrast, in mice with proteinuria, where the glomerular filtration barrier is disorganized, the amount of nanoparticles in the glomerular compartment is strongly increased, revealed by a strong expression of eGFP (FIG. 7D).

CONCLUSION

The new nanoparticle system of the invention is able to deliver therapeutic DNA molecules into cells. It has been demonstrated that these nanoparticles enter at low level in not treated cells and in high amount in damaged cells. It has also been demonstrated that the nanoparticles are able to reach the glomerular compartment in the kidney of mice with proteinuria. The nanoparticles are able to promote the expression of a selected protein (eGFP) in parallel with the expression of iRNAs. This property makes the nanoparticles of the invention able not only to inhibit the expression of pathological proteins but also to be useful for the degradation of an inactive mutated protein and its replacement by an active one. As examples of a therapeutic use of nanoparticles of the invention: a treatment for INS by inhibiting Cmip expression in the podocytes using an iRNA expressing vector with a podocyte specific promoter and also a treatment for the nephrotic syndromes with genetic origins, using a vector expressing an iRNA targeting the mutated protein and expressing an active protein using an iRNA resistant sequence.

The invention claimed is:

1. A nanoparticle comprising a nanoparticle core and a multilayered shell, wherein:
said multilayer shell is composed of a least one alternate bilayer of one positively charged layer comprising at least one chitosan derivative and one negatively charged layer comprising or consisting of at least one non-viral expression DNA vector,
where the outer layer of said multilayer shell is a positively charged layer comprising said at least one chitosan derivative, and
said chitosan derivatives of the multilayer shell are thiolated chitosan derivatives,
and wherein the nanoparticle core is hollow or comprises a material selected from the group consisting of metals; metal-coated materials; metal oxides; plastics; ceramics; silicon; glasses; mica; graphite; hydrogels; polymers and combinations thereof,
and wherein said non-viral expression DNA vector encodes at least one interfering RNA capable of silencing CMIP, and/or at least one protein of interest or at least one additional interfering RNA targeting a different target gene sequence.

2. A nanoparticle of claim 1, where the nanoparticle core is hollow or comprises a material selected from the group consisting of gold, silver, platinum, aluminum, and combinations thereof.

3. A nanoparticle of claim 1, where the DNA expression vectors express at least one interfering RNA capable of silencing a mutated protein and express a corresponding functional protein which is encoded by a sequence to which said interfering RNAs do not bind, and wherein the protein is a protein of kidney slit diaphragm.

4. A nanoparticle of claim 1, wherein the nanoparticle size is in the range of 10 nm-1 μm.

5. A nanoparticle of claim 1, wherein the number of negatively charged layers ranges from 1-15.

6. A pharmaceutical composition comprising at least one nanoparticle and a pharmaceutically acceptable carrier, wherein the nanoparticle comprises a nanoparticle core and a multilayered shell, wherein:
said multilayer shell is composed of a least one alternate bilayer of one positively charged layer comprising at least one chitosan derivative and one negatively charged layer comprising or consisting of at least one non-viral expression DNA vector,
where the outer layer of said multilayer shell is a positively charged layer comprising said at least one chitosan derivative, and
said chitosan derivatives of the multilayer shell are thiolated chitosan derivatives,
and wherein the nanoparticle core is hollow or comprises a material selected from the group consisting of metals; metal-coated materials; metal oxides; plastics; ceramics; silicon; glasses; mica; graphite; hydrogels; polymers and combinations thereof,
and wherein said non-viral expression DNA vector encodes at least one interfering RNA capable of silencing CMIP, and/or at least one protein of interest or at least one additional interfering RNA targeting a different target gene sequence.

7. A method for the preparation of a nanoparticle, comprising:
a. providing a core nanoparticle, as a template, that comprises or consists of a material selected from the group consisting of metals, metal-coated materials, metal oxides, plastics, ceramics, silicon, glasses, mica, graphite, hydrogels, polymers and combinations thereof,
b. at least one step of layer-by-layer depositing alternatively a positively charged layer comprising at least one chitosan derivative and a negatively charged layer consisting of at least one non-viral expression DNA vector, on the surface of the core of step (a) to provide a polyelectrolyte assembly coating on the surface of the core, where the last deposited layer is a positively charged layer comprising said at least one chitosan derivative,
where said chitosan derivatives of the polyelectrolyte assembly are thiolated chitosan derivatives or a mixture of thiolated chitosan derivatives and non thiolated chitosan derivatives,
c. optionally, removal of the material of step (a).

8. A method for the preparation of a nanoparticle of claim 7, where the first step of (b) is a step of depositing a positively charged layer comprising at least one chitosan derivative on the surface of the core of step (a), to provide a first layer coating on the surface of the core, followed by a step of depositing a negatively charged layer comprising at least one non-viral expression DNA vector, optionally said two steps can be reiterated alternatively, and where the last deposited layer is a positively charged layer comprising said at least one chitosan derivative.

9. A method for the preparation of a nanoparticle of claim 7, where the thiolated chitosan derivatives are previously prepared by reacting chitosan derivatives with iminothiolane or by oxidation reaction of chitosan followed by reductive amination.

* * * * *